United States Patent
Yoko et al.

(10) Patent No.: US 10,987,225 B2
(45) Date of Patent: Apr. 27, 2021

(54) SYSTEMS AND METHODS FOR ATTACHING SLEEVE OR CONE IN PROSTHETIC IMPLANT HAVING A STEM

(71) Applicant: Zimmer, Inc., Warsaw, IN (US)

(72) Inventors: Tim Yoko, Granger, IN (US); Amanda Szalkowski, Winona Lake, IN (US)

(73) Assignee: Zimmer, Inc., Warsaw, IN (US)

( * ) Notice: Subject to any disclaimer, the term of this patent is extended or adjusted under 35 U.S.C. 154(b) by 39 days.

(21) Appl. No.: 16/047,463

(22) Filed: Jul. 27, 2018

(65) Prior Publication Data
US 2019/0038417 A1 Feb. 7, 2019

Related U.S. Application Data (60) Provisional application No. 62/541,267, filed on Aug. 4, 2017.

(51) Int. Cl.
*A61F 2/30* (2006.01)
*A61F 2/38* (2006.01)

(52) U.S. Cl.
CPC .......... *A61F 2/30734* (2013.01); *A61F 2/389* (2013.01); *A61F 2/3859* (2013.01);
(Continued)

(58) Field of Classification Search
CPC .............. A61F 2/30734; A61F 2/30736; A61F 2/30738; A61F 2/3868; A61F 2/389;
(Continued)

(56) References Cited

U.S. PATENT DOCUMENTS

| 5,282,861 A | 2/1994 | Kaplan |
| 5,702,461 A * | 12/1997 | Pappas ............... A61F 2/389 |
| | | 623/20.34 |

(Continued)

FOREIGN PATENT DOCUMENTS

| WO | 2014063084 | 4/2014 |
| WO | 2019075066 | 4/2019 |
| WO | 2019075078 | 4/2019 |

OTHER PUBLICATIONS

Smith & Nephew Legion Cones Surgical Technique V1 (Jan. 2017) (Year: 2017).*

(Continued)

*Primary Examiner* — Brian A Dukert
*Assistant Examiner* — Rebecca Lynee Zimmerman
(74) *Attorney, Agent, or Firm* — Schwegman Lundberg & Woessner, P.A.

(57) ABSTRACT

A prosthetic implant system for reconstructing a knee joint comprises a prosthetic implant and sleeve. The prosthetic implant comprises a tibial tray component for reconstructing a tibia of the knee joint, and a stem configured to extend from the tibial tray component to anchor the tibial tray component in the tibia of the knee joint. The sleeve comprises an outer wall configured to engage with bone, and an inner bore configured to receive the stem. The inner bore is shaped to couple to the prosthetic implant at a first location proximate the tibial tray component while surrounding the stem, and uncouple from the prosthetic implant at a second location spaced from the first location while still surrounding the stem. Methods employing the prosthetic implant system can comprise intraoperatively determining to use the sleeve in a coupled or un-coupled configuration based on a depth of a broach into a broached channel.

19 Claims, 5 Drawing Sheets

(52) U.S. Cl.
CPC ............... *A61F 2002/30332* (2013.01); *A61F 2002/30604* (2013.01); *A61F 2002/30738* (2013.01); *A61F 2002/30884* (2013.01)

(58) Field of Classification Search
CPC .......... A61F 2/3859; A61F 2002/30332; A61F 2002/30884; A61F 2002/30604
See application file for complete search history.

(56) References Cited

U.S. PATENT DOCUMENTS

| | | | |
|---|---|---|---|
| 6,911,100 B1 | 6/2005 | Gibbs et al. | |
| 7,291,174 B2 * | 11/2007 | German | A61F 2/30734 623/20.15 |
| 8,535,385 B2 * | 9/2013 | Hanssen | A61F 2/34 623/23.19 |
| 8,721,733 B2 | 5/2014 | Bonitati | |
| 2005/0124998 A1 | 6/2005 | Coon et al. | |
| 2012/0143204 A1 | 6/2012 | Blaylock et al. | |
| 2012/0310246 A1 | 12/2012 | Belcher et al. | |
| 2013/0172892 A1 | 7/2013 | Servidio et al. | |
| 2013/0325019 A1 | 12/2013 | Thomas et al. | |
| 2014/0228846 A1 | 8/2014 | Roby et al. | |
| 2014/0277528 A1 | 9/2014 | Mines et al. | |
| 2014/0277540 A1 | 9/2014 | Leszko et al. | |
| 2014/0277546 A1 | 9/2014 | Major | |
| 2015/0216667 A1 | 8/2015 | Monaghan | |
| 2016/0081758 A1 | 3/2016 | Bonutti | |
| 2016/0367381 A1 | 12/2016 | Chaney et al. | |
| 2017/0000503 A1 | 1/2017 | Keefer et al. | |
| 2019/0105159 A1 * | 4/2019 | Dees | A61F 2/30734 |
| 2019/0110906 A1 | 4/2019 | Yoko et al. | |
| 2019/0110907 A1 | 4/2019 | Yoko et al. | |
| 2020/0289290 A1 | 9/2020 | Yoko et al. | |

OTHER PUBLICATIONS

"International Application Serial No. PCT US2018 055218, International Search Report dated Jan. 30, 2019", 5 pgs.

"International Application Serial No. PCT US2018 055218, Written Opinion dated Jan. 30, 2019", 5 pgs.

"International Application Serial No. PCT US2018 055232, Invitation to Pay Additional Fees and Partial Search Report dated Jan. 24, 2019", 14 pgs.

"International Application Serial No. PCT US2018 055232, International Search Report dated Mar. 19, 2019", 8 pgs.

"International Application Serial No. PCT US2018 055232, Written opinion dated Mar. 19, 2019", 12 pgs.

"U.S. Appl. No. 16/652,896, Preliminary Amendment Filed Apr. 1, 2020", 8 pgs.

"International Application Serial No. PCT/US2018/055218, International Preliminary Report on Patentability dated Apr. 23, 2020", 7 pgs.

"International Application Serial No. PCT/US2018/055232, International Preliminary Report on Patentability dated Apr. 23, 2020", 12 pgs.

"European Application Serial No. 187962303, Response to Communication pursuant to Rules 161(1) and 162 EPC filed Nov. 30, 20", 22 pages.

"European Application Serial No. 18797274.0, Response to Communication pursuant to Rules 161(1) and 162 EPC filed Dec. 8, 20", 18 pages.

"U.S. Appl. No. 16/156,728, Response filed Oct. 12, 20 to Restriction Requirement dated Aug. 21, 2020"9 pages.

"U.S. Appl. No. 16/156,747, Non Final Office Action dated Oct. 21, 2020"9 pages.

* cited by examiner

SYSTEMS AND METHODS FOR ATTACHING SLEEVE OR CONE IN PROSTHETIC IMPLANT HAVING A STEM

CLAIM OF PRIORITY

This application claims the benefit of U.S. Provisional Patent Application Ser. No. 62/541,267, filed on Aug. 4, 2017, the benefit of priority of which is claimed hereby, and which is incorporated by reference herein in its entirety.

TECHNICAL FIELD

This document pertains generally, but not by way of limitation, to prosthetic implant devices having stems configured to be inserted into bone. More specifically, but not by way of limitation, the present application relates to coupling and mounting of sleeves and cones to the tibial or femoral devices for implantation in the bone.

BACKGROUND

Prosthetic implant devices, such as femoral and tibial components, sometimes include a stem extending from a bearing component such as a tibial tray. The stem can extend along a length of the diaphysis portion of the tibia, while the tray can be configured to abut a resected portion of the epiphysis portion of the tibia configured to mate with the femur. Sometimes the metaphysis portion of the tibia below the epiphysis includes damaged or unhealthy cancellous bone at the resection. As such, it is sometimes desirable to remove weakened bone material, such as with a broach or reamer, to leave a space in the metaphyseal portion of the bone larger than the stem. Sometimes a sleeve is mechanically coupled to a tibial or femoral component in order to fill the space.

Examples of sleeves for use with prosthetic implants are described in U.S. Pat. No. 8,721,733 to Bonitati; U.S. Pub. No. 2014/0277528 to Mines et al.; U.S. Pub. No. 2014/0277540 to Leszko et al.; and U.S. Pub. No. 2017/0000503 to Keefer et al.

Overview

The present inventors have recognized, among other things, that a problem to be solved can include over-broaching of the metaphysis of a long bone, such as a tibia. Over-broaching of the metaphysis can result in forming a broached channel within the metaphysis that is deeper than desired. For example, it is desirable that a sleeve for a stem of a tibial implant can be located at or just below a resected tibial surface to, among other things, increase bone ingrowth and reduce void space within the bone and also to be seated on rigid cancellous or cortical bone. In such a configuration, the sleeve can be attached to the tibial tray stem housing for positioning close to the tibial tray, near the resected tibial surface. However, if the broach or reamer is operated or otherwise inserted too far along the axis of the bone, or if the bone quality is too poor to support the sleeve at the intended position, a gap between the sleeve and the broached channel can arise, which would eliminate sufficient axial support and also inhibit boney ingrowth into the porous sleeve material. Often times, the gap can be eliminated by further resecting the bone so that the broached channel is below the finally resected surface at the desirable depth so that the sleeve can contact the cancellous bone in the intramedullary canal. This, however, can result in undesirable loss of healthy bone and can require the use of additional components, such as spacers and the like.

The present subject matter can help provide a solution to this problem, such as by converting or otherwise using a coupled sleeve for a tibial or femoral implant as an uncoupled cone that is detached from, but still surrounding, the tibial or femoral stem housing. The sleeve can be pushed down into the broached channel to engage bone and the tibial stem can be inserted therethrough. Any gaps or voids between the sleeve and the tibial tray can be filled with bone cement. A surgeon can intraoperatively evaluate the broached channel and determine if the sleeve should be used attached to the stem housing of the tibial tray or if the sleeve should be used as an uncoupled cone and inserted into the broached channel to be separated from the tibial tray stem housing and seated into the metaphyseal bone. The sleeve, when used as a cone, can include additional features, such as bone cement cavities, to facilitate attachment to the intramedullary canal through bone cement.

In an example, a prosthetic implant system for at least partially reconstructing a knee joint can comprise a prosthetic implant and sleeve. The prosthetic implant can comprise a tibial tray component for at least partially reconstructing a tibia of the knee joint, and a stem configured to extend from the tibial tray component to anchor the tibial tray component in the tibia of the knee joint. The sleeve can comprise an outer wall configured to engage with bone, and an inner bore configured to receive the stem. The inner bore can be shaped to couple to the prosthetic implant at a first location proximate the tibial tray component while surrounding at least a portion of the stem, and uncouple from the prosthetic implant at a second location spaced from the first location while still surrounding at least a portion of the stem.

In another example, a method of implanting an implant including a stem can comprise reaming an intramedullary canal of a long bone to form a channel, resecting an epiphysis portion of the long bone to form a resected surface, broaching a proximal end of the long bone to form a broached channel, evaluating a depth of the broach below the resected surface, determining to use a stem sleeve in a coupled or un-coupled state based on the depth of the broach, inserting the stem sleeve into the broached channel for the un-coupled state or attaching the stem sleeve onto the stem of the implant for the coupled state, and inserting the implant into the broached channel.

This overview is intended to provide an overview of subject matter of the present patent application. It is not intended to provide an exclusive or exhaustive explanation of the invention. The detailed description is included to provide further information about the present patent application.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
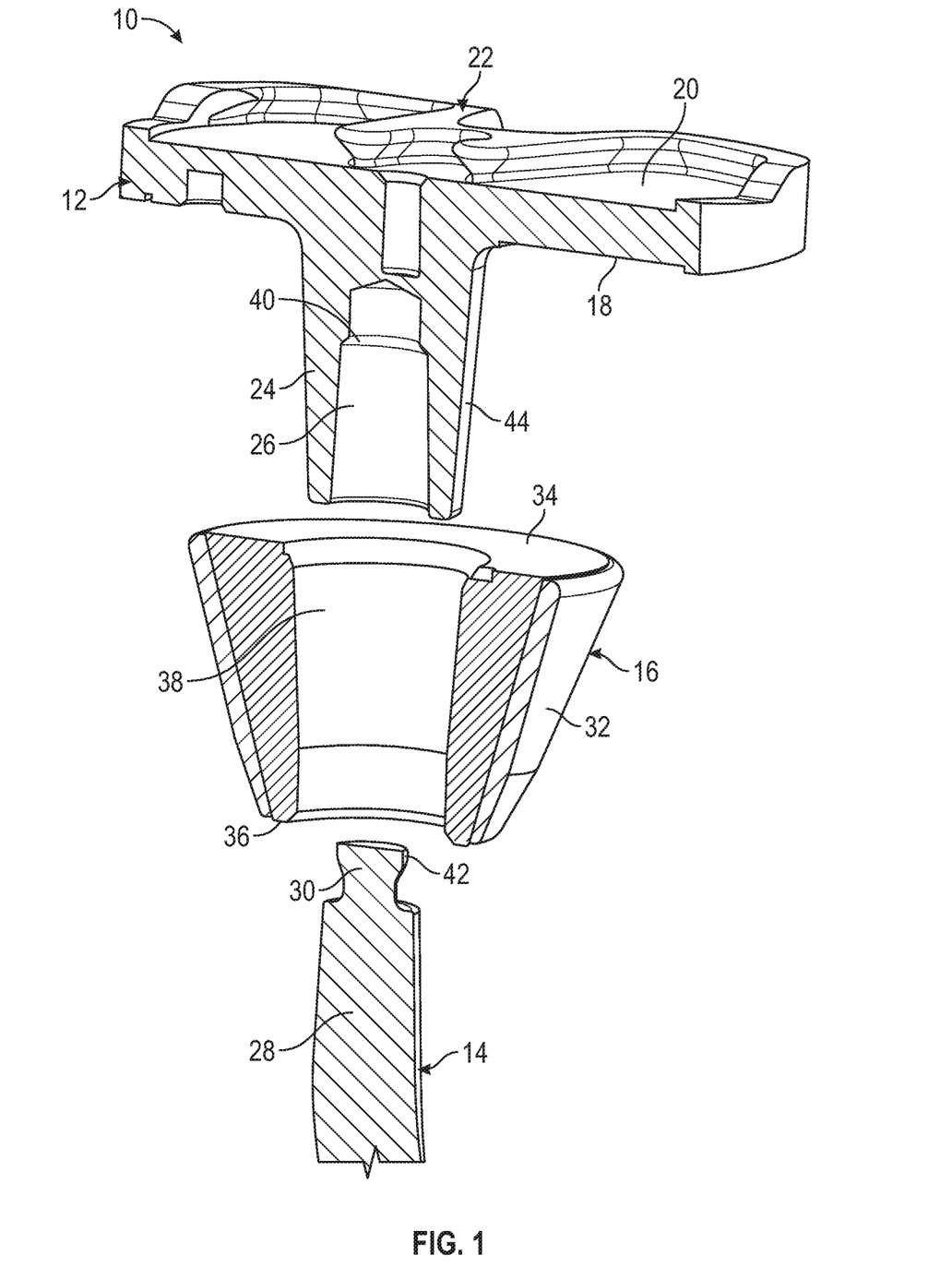
FIG. 1 is an exploded perspective view of a tibial component having a tibial stem with a sleeve configured to be disposed to surround the tibial stem housing.

FIG. 1 is an exploded perspective view of tibial construct or component 10 having tibial tray 12, tibial stem 14 and sleeve 16. Tibial tray 12 can comprise bone-facing surface 18, bearing surface 20, retaining features 22, stem housing 24 and stem housing socket 26. Tibial stem 14 can comprise shaft portion 28 and lockdown post 30. Sleeve 16 can comprise exterior surface 32, proximal portion 34, distal portion 36 and interior channel 38.

Figure 4:
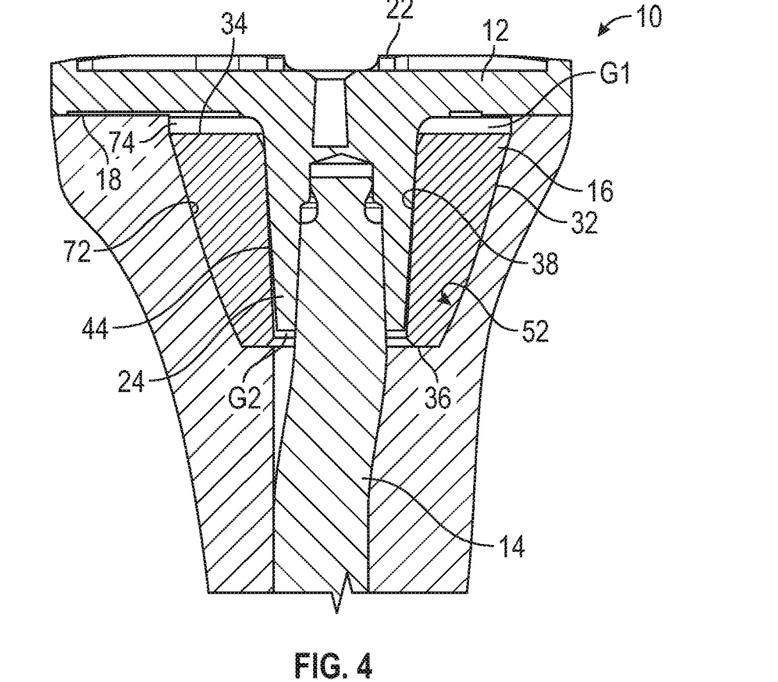
FIG. 4 is a side cross-sectional view of the tibial component and sleeve of FIG. 1 inserted into the broached intramedullary canal of FIG. 3 in a coupled configuration.

Tibial stem 14 is configured to be attached to tibial tray 12 and sleeve 16 is configured to surround tibial stem 14 and stem housing 24. Lockdown post 30 of tibial stem 14 can be inserted into stem housing socket 26 of tibial tray 12. Stem housing socket 26 can include lip 40 that can engage head 42 of lockdown post 30 to hold tibial stem 14 within stem housing socket 26. Outer surface 44 of stem housing 24 and interior channel 38 of sleeve 16 can be configured to engage each other to secure sleeve 16 to tibial tray 12. As explained in greater detail below, in an embodiment, outer surface 44 can be configured to have a Morse taper and interior channel 38 can be configured to have a corresponding shape to seat on the Morse taper of outer surface 44, as shown in FIG. 4. Retaining features 22 can be used to secure various bearing components against bearing surface 20 of tibial component 10 to engage a femoral component. For example, retaining features 22 can include flanges having lips into which mating components of mobile or fixed bearings can be fitted to engage condylar surfaces of a femoral component.

Tibial stem 14 is configured to be pushed down into an intramedullary canal of a tibia bone to anchor tibial tray 12 so that bone-facing surface 18 contacts a resected bone surface of the tibia. Furthermore, sleeve 16 can be positioned around stem housing 24 to provide additional anchoring. For example, tibial stem 14 can be inserted into one or both of cancellous and cortical bone and sleeve 16 can be pushed into engagement with one or both of cancellous and cortical bone. Exterior surface 32 can be porous to promote bone in-growth, as discussed in greater detail below. The systems, devices and methods of the present application permit sleeve 16 to be implanted into a tibia in conjunction with tibial tray 12 and tibial stem 14 in different configurations to accommodate tibia bones that have been reamed, broached or resected with varying geometries. A surgeon can intraoperatively decide to attach sleeve 16 to stem housing 24 for a broaching channel that is shallow or can intraoperatively decide to push sleeve 16 into a deep broaching channel without attachment to tibial stem 14. Furthermore, different configurations of sleeve 16, e.g., configurations with indentations or projections, can be provided to accommodate different bone geometries achieved via one or more of reaming, broaching and resecting in attached and unattached configurations.

Figure 2:
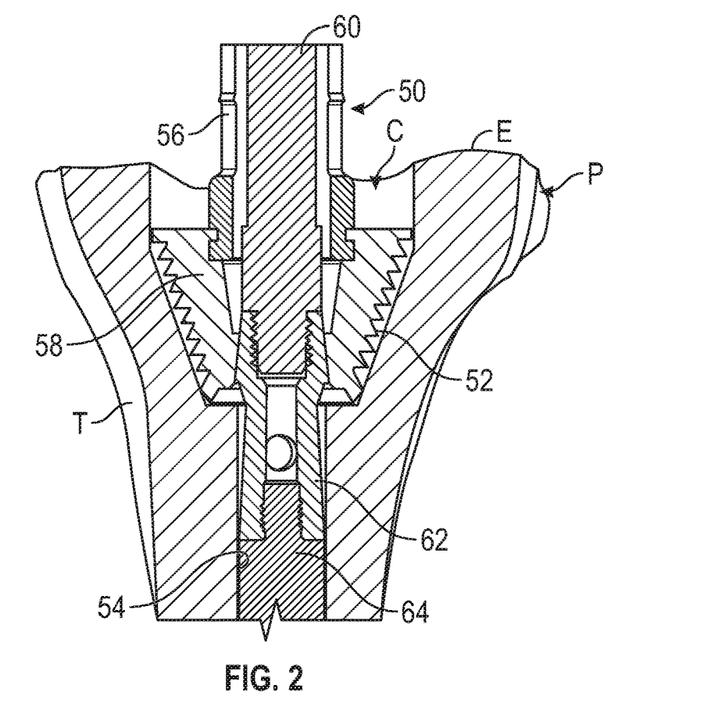
FIG. 2 is a side cross-sectional view of a proximal end of a tibia having a broaching tool inserted into the metaphysis via the intramedullary canal of the tibia to form a broaching channel.

FIG. 2 is a side cross-sectional view of proximal end P of tibia T having broaching tool 50 inserted into metaphysis region of tibia T along an axis extending along intramedullary canal C of tibia T to form broaching channel 52. Reaming channel 54 can also extend along the axis of intramedullary canal C. Broaching tool 50 can comprise broach shaft 56 and broach 58. Broach shaft 56 and broach 58 can be cannulated to include an internal passage that receives stem extension post 60, which is connected to offset or straight stem provisional 62 and extension post 64. In other embodiments, stem provisional 62 and extension post 64 can be combined into a single piece.

With broach 58 inserted into tibia T, broach shaft 56 can be reciprocated in an up-and-down motion relative to the orientation of FIG. 1 to widen reaming channel 54 along the axis of intramedullary canal C. As shown in FIG. 2, broach 58 can include various cutting surfaces, serrations, edges or the like to chip away, cut away or otherwise remove bone. In embodiments, broach 58 can be inserted into reaming channel 54 to widen reaming channel 54 into broaching channel 52. Reaming channel 54 can be produced using a reamer in any suitable manner before or after broaching tool 50 is used to form broaching channel 52.

Reaming channel 54 can comprise a generally cylindrical shaped passage extending longitudinally along an axis of tibia T. Reaming channel 54 can extend into and through cancellous bone of tibia T. The cancellous bone of tibia T is surrounded by an outer layer of harder cortical bone. Reaming channel 54 can form a passage for receiving a tibial post or stem that extends from a tibial component. For example, straight or offset stem provisional 62 and extension post 64 can be inserted into reaming channel 54. Furthermore, tibial stem 14 of FIG. 1 can be inserted into reaming channel 54 after trialing and straight or offset stem provisional 62 and extension post 64 are removed. Tibial stem 14 can provide anchoring of tibial component 10 to tibia T.

Tibial component 10 can be further anchored to tibia T using sleeve 16 of FIG. 1. Broaching channel 52 can comprise a widened and tapered portion of reaming channel 54 shaped to receive sleeve 16. Broach 58 can have the same outer angular dimensions as sleeve 16. That is, the angles of the side walls relative to the inferior and superior wall can be the same. However, as discussed below, broach 58 can be taller than sleeve 16. Thus, when broaching tool 50 is removed from tibia, broaching channel 52 can be configured to mate with sleeve 16. However, sometimes it is possible for broach 58 to advance too far down into intramedullary canal C such that broaching channel 52 is positioned too far below epiphysis end E of tibia T.

Figure 3:
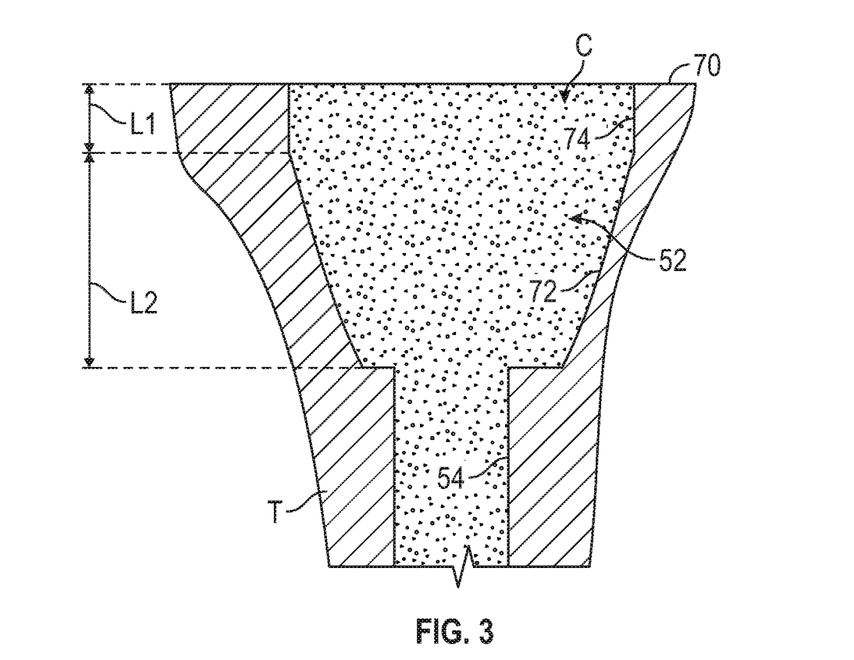
FIG. 3 is a side cross-sectional view of the proximal end of the tibia of FIG. 2 with the broaching tool removed and an epiphysis region of the bone resected at a resected surface.

FIG. 3 is a side cross-sectional view of the proximal end of tibia T of FIG. 2 with broaching tool 50 removed and epiphysis end E of tibia T resected at resected surface 70. Broaching channel 52 can include tapered portion 72 and longitudinal portion 74. Longitudinal portion 74 can have length L1, which can be measured from resected surface 70. In other words, tapered portion 72 can begin a distance equal to length L1 below resected surface 70. Tapered portion 72 can have a longitudinal length L2 equivalent to the height of broach 58. Additionally, the angle between longitudinal portion 74 and tapered portion 72 can match with the geometer of broach 58. After broaching with broach 58, epiphysis E is resected to provide a planar, or nearly planar, surface for engaging flush with tibial tray 12 (FIG. 1) at resected surface 70. Additionally, resectioning of tibia T can be performed prior to broaching.

For the coupled configuration, as discussed below, the length of L1 can be close to zero and a gap for bone cement between sleeve 16 and tibial tray 12 (FIG. 1) can be produced by the difference in height of broach 58 and sleeve 16. For the un-coupled configuration, the gap for bone cement will increase, beyond the difference in height of broach 58 and sleeve 16, by the additional length of L1 beyond what is desirable for the coupled configuration. For the un-coupled configuration, the length of L1 can be in the range of 0.5 to 2.5 millimeters. In an example embodiment, length L1 is 1.5 millimeters. Such a range has been found to allow for an adequate amount of bone cement to provide suitable adhesion.

For the coupled configuration, it is desirable to maintain length L1 as small as practical in order to allow sleeve 16 to engage bone within broaching channel 52, which can be achieved by broaching tibia T so that the proximal or superior surface of broach 58 (FIG. 2) is flush with surface 70. If length L1 is too large, when sleeve 16 is coupled to stem housing 24, sleeve 16 will not engage bone down in broaching channel 52 because tibial tray 12 will prevent sleeve 16 from advancing downward. Thus, if length L1 is too large, previously it would be necessary to remove more of epiphysis E to allow a sleeve to contact bone and a thicker tibial tray, or a spacer, would be used to provide additional length to the repaired tibia. The systems, devices and methods of the present application permit a surgeon to utilize sleeve 16 in a first configuration if length L1 is in a close to zero, e.g., 0.5 mm and below, or use sleeve 16 in a second configuration if length L1 is within a desired range, e.g., 0.5 mm to 2.5 mm. Additionally, the present application includes sleeves 16 of different configurations that can be used for different values of length L1. Thus, healthy bone at epiphysis E does not need to be removed and sleeve 16 can achieve contact with cancellous or cortical bone to promote bone ingrowth and stabilization of tibial component 10.

As such, the resection of bone of tibia T is conducted so as to be commensurate with using a coupled sleeve to keep length L1 small and preserve bone. Thereafter, if it is determined that bone within longitudinal portion 74 is unhealthy and cannot support a coupled sleeve or if it is determined that length L1 is to large to facilitate contact of a sleeve to both the tibial component and bone, a sleeve can be used in an uncoupled state. Thus, a surgeon can intraoperatively decide to switch from initially using a sleeve in a coupled state to using a sleeve in an uncoupled state or a cone. In order to facilitate such a configuration, additional broaching can be conducted to, for example, position the sleeve below unhealthy bone. However, further resectioning is avoided to preserve cortical bone and avoid use of a spacer or thicker tibial tray.

FIG. 4 is a side cross-sectional view of tibial component 10 and sleeve 16 of FIG. 1 inserted into broached intramedullary canal C of FIG. 3 in a coupled configuration. In the configuration of FIG. 4, sleeve 16 is attached to stem housing 24. Sleeve 16 can be attached to stem housing 24 in a variety of configurations, such as via threaded engagement, ribbed coupling (e.g., where shallow ribs on stem housing 24 engage with shallow ribs on sleeve 16), snap fit, force fit, press fit, Morse taper, or via use of additional fasteners. In the illustrated embodiment, sleeve 16 is attached to stem housing 24 via Morse taper. In examples, outer surface 44 of stem housing 24 is configured to have a Morse taper and interior surface 38 of sleeve 16 is configured to have a mating recess such that a self-holding connection is made. Such a configuration is discussed in greater detail in U.S. Pat. No. 6,911,100 to Gibbs et al., which is hereby incorporated by reference in its entirety for all purposes. In other examples, other tapered connections can be used, such as described in U.S. Pub. No. 2015, 0216667 to Monaghan, which is hereby incorporated by reference in its entirety for all purposes. In yet other examples, sleeve 16 can be coupled to bone-facing surface 18 rather than stem housing 24.

With sleeve 16 connected to stem housing 24, sleeve 16 contacts tibia T at tapered portion 72 of broaching channel 52. Longitudinal portion 74 is small to permit exterior surface 32 to engage tapered portion 72 while still allowing gap G1 to be present between bone-facing surface 18 of tibial tray 12 and proximal portion 34 of sleeve 16. Gap G1 can be filled with bone cement. For example, gap G1 and broaching channel 52 can be filled with bone cement prior to insertion of tibial stem 14 into broaching channel 52. This can permit gap G2 along distal portion 36 to fill with bone cement.

Figure 5:
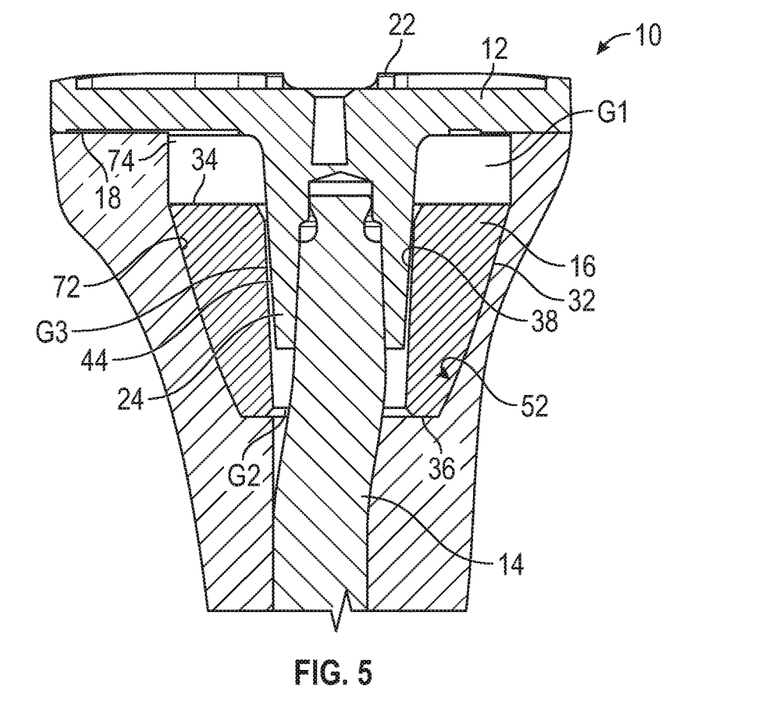
FIG. 5 is a side cross-sectional view of the tibial component and sleeve of FIG. 1 inserted into the broached intramedullary canal of FIG. 3 in an un-coupled configuration to act as a cone.
Figure 6:
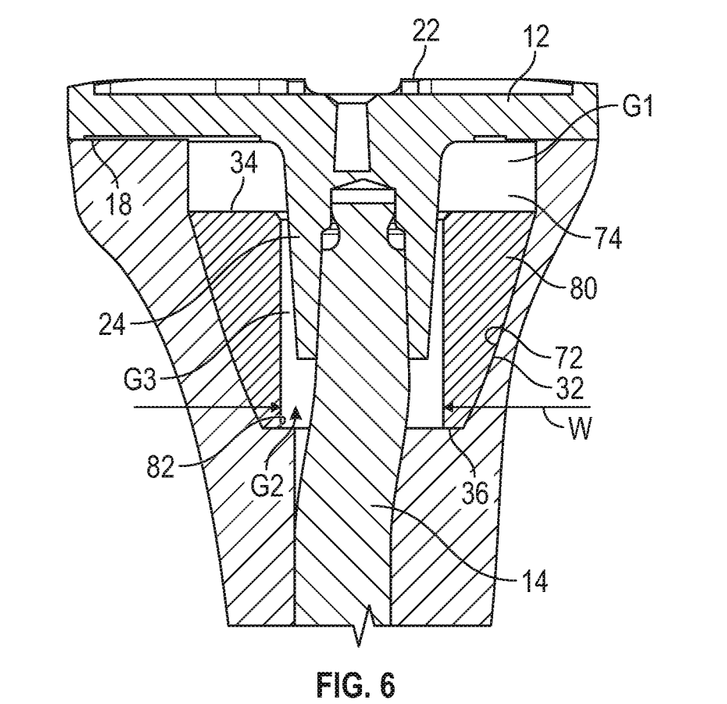
FIG. 6 is a side cross-sectional view of another embodiment of an un-coupled sleeve acting as an un-coupled cone having a through-bore for surrounding a tibial stem.

If length L1 is determined to be larger than will permit sleeve 17 to contact tibia T, a surgeon can intraoperatively decide to install sleeve 16 in an un-coupled configuration, as shown in FIG. 5, or install an altogether different device, such as uncoupled sleeve or cone 80 of FIG. 6.

FIG. 5 is a side cross-sectional view of tibial component 10 and sleeve 16 of FIG. 1 inserted into broached intramedullary canal C of FIG. 3 in an un-coupled configuration. In the configuration of FIG. 5, sleeve 16 is not attached to stem housing 24. In such a configuration (e.g., unattached to stem housing 24), sleeve 16 can be referred to as a cone.

Sleeve 16 is configured to be pushed into intramedullary canal C to contact tapered portion 72 without being connected to stem housing 24. Thus, sleeve 16 can contact tibia T at tapered portion 72 of broaching channel 52. Longitudinal portion 74 is large so that sleeve 16 cannot be connected to stem housing 24 and maintain contact with tapered portion 72. Thus, sleeve 16 is first inserted into intramedullary canal C and tibial stem 14 is subsequently inserted into interior channel 38 of sleeve 16 without contacting sleeve 32. Sleeve 16 still, at least partially, surrounds stem housing 24 and tibial stem 14, but further distally down along the lengths of stem housing 24 and tibial stem 14, particularly along a portion where interior channel 38 will not attach to outer surface 44. Gap G1 can be formed between bone-facing surface 18 of tibial tray 12 and proximal portion 34 of sleeve 16. Gap G2 can be filled with bone cement. Furthermore, bone cement can be applied to gap G3 between interior channel 38 of sleeve 16 and outer surface 44 stem housing 24.

Use of sleeve 16 in an un-attached configuration, such as is shown in FIG. 5, permits tibial component 10 to be used without modification for larger sized lengths L1, and prevents having to perform additional modification to tibia T, thereby preserving bone matter. Likewise, sleeve 16 can be used without modification. As such, fewer components need to be maintained in a hospital inventory. However, in other embodiments of the present application, sleeve 16 can be modified or a different sleeve can be used. As shown in FIG. 6, a sleeve of the present application can be configured to increase the size of gap G3 to allow for a larger volume of bone cement and to prevent interference with stem housing 24.

FIG. 6 is a side cross-sectional view of un-coupled sleeve or cone 80 having through-bore 82 for surrounding tibial stem 14. Cone 80 is similar to sleeve 16 except that interior channel 38 is replaced with through-bore 82. All other elements are labeled with like reference numbers. Thus, cone 80 can comprise exterior surface 32, proximal portion 34, distal portion 36 and through-bore 82. Through-bore 82 can have a larger diameter or width W than interior channel 38. Width W can be uniform between proximal portion 34 and distal portion 36 to have a cylindrical shape. As such, through-bore 82 does not have a taper that matches tapering of stem housing 24. Furthermore, width W can be larger than the outer width of stem housing 24 such that gap G2 can be larger than in FIG. 6 to accept more bone cement and to prevent interference between stem housing 24 and cone 80. Thus, through-bore 82 can be sized to not attach to stem housing 24 so that cone 80 cannot be used in the attached or coupled configuration, in various examples.

Sleeve 16 and cone 80 can provide engagement with tapered portion 72 such as by flush contact or a force fit. Tibial component 10 can be anchored to sleeve 16 and cone 80 within tibia T using bone cement to anchor tibial component 10 to tibia T. Thus, sleeve 16 and cone 80 can still be used to take up the space of removed unhealthy bone, but can be firm or rigid to prevent or inhibit movement of tibial component 10. Also, sleeve 16 and cone 80 can include various features, such as exterior sockets, that can receive bone cement to provide additional stabilizing, and sleeve 16 and cone 80 can be made of a porous material to promote bone in-growth, as discussed in detail with reference to FIG. 7.

Figure 7:
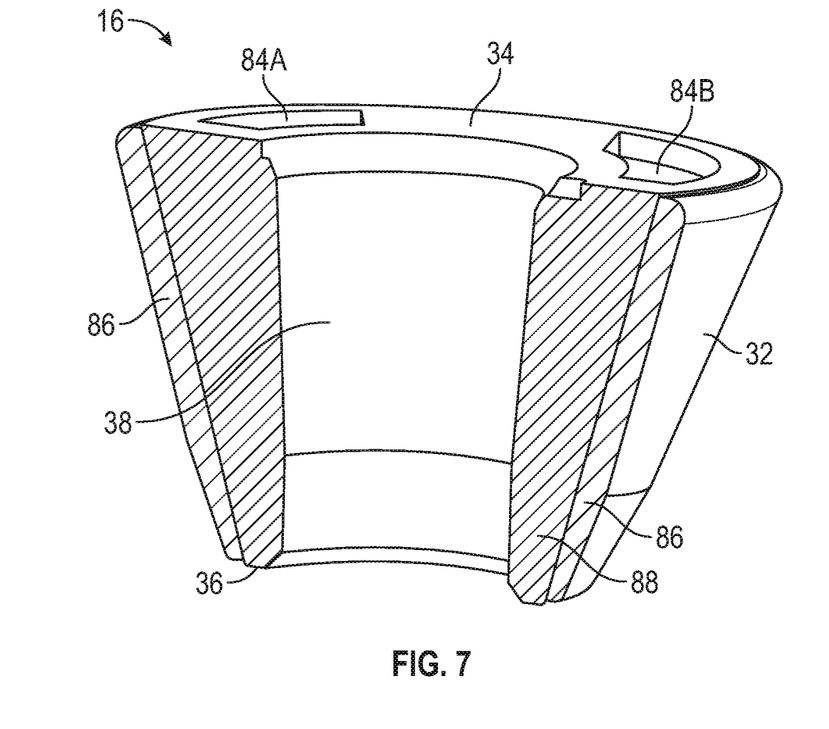
FIG. 7 is a perspective cross-sectional view of another embodiment of the sleeve of FIGS. 4 and 5 showing surface indentations configured to receive bone cement.

FIG. 7 is a perspective cross-sectional view of another embodiment of un-coupled sleeve 16 of FIG. 4 showing surface indentations 84A and 84B that are configured to receive bone cement. FIG. 7 also shows sleeve 16 including outer porous layer 86 and inner core layer 88. Indentations 84A and 84B can be included in proximal portion 34 to receive bone cement that is delivered to or otherwise positioned on sleeve 16. Indentations 84A and 84B can allow solidified bone cement to further hold sleeve 16 in place within tapered portion 72 of tibia T. For example, indentations 84A and 84B can provide anti-rotation attributes to sleeve 16 (in combination with solidified bone cement), which can be particularly useful in the un-coupled configuration where sleeve 16 is not separately provided with anti-rotation benefits from being coupled to stem housing 24. Indentations 84A and 84B can have a variety of cross-sectional shapes, such as circular, oval, square, rectangular, etc. In various examples, indentations 84A and 84B can have shapes that follow the shape of exterior surface 32 and through-bore 82. Thus, for example, indentations 84A and 84B can be arcuate or claw-shaped to fit between the circular shape of through-bore 82 and the oval shape of exterior surface 32. The various claw shapes can have two opposing curved surfaces that that can be connected by one or two straight or curved end surfaces.

Sleeve 16 and cone 80 can be fabricated from a variety of different materials and layers. Sleeve 16 and cone 80 can be fabricated of porous material as previously described. In examples, sleeve 16 and cone 80 can be fabricated from biocompatible metals such as titanium or cobalt chrome. In other examples, sleeve 16 and cone 80 can be fabricated from porous metal structures. As shown in FIG. 7, sleeve 16 and cone 80 can also be made of a combination of materials disposed in a combination of layers. For example, core layer 88 can be made of a solid material that provides a smooth surface at interior channel 38. This can permit interior channel 38 to form a strong contact within the Morse taper connection. Outer porous layer 86 can be made of material having voids to promote bone ingrowth.

Sleeve 16 and cone 80 in their entirety or outer porous layer 86 can be formed of a suitable material that promotes bone ingrowth and is biocompatible, such as porous metal, or a porous tantalum having a porosity as low as 55%, 65%, or 75% and as high as 80%, 85%, or 90%, for example. An example of a highly porous tantalum material is produced using Trabecular Metal™ Technology generally available from Zimmer Biomet, of Warsaw, Ind. Trabecular Metal™ is a trademark of Zimmer Biomet. Such a material may be formed from a reticulated vitreous carbon foam substrate which is infiltrated and coated with a biocompatible metal, such as tantalum, by a chemical vapor deposition (CVD) process in the manner disclosed in detail in U.S. Pat. No. 5,282,861 to Kaplan, the disclosure of which is expressly incorporated herein by reference in its entirety for all purposes. In addition to tantalum, other metals such as niobium, or alloys of tantalum and niobium with one another or with other metals may also be used. Sleeve 16 can comprise an open cell tantalum structure. Highly porous material can have open cell metal structures that can be fabricated using a tantalum metal film and a carbon substrate combination, with the film deposited by CVD, which mimics bone closely in having ligaments interconnected to form open spaces.

In addition to indentations 84A and 84B, sleeve 16 can include other fixation features that can facilitate attachment of sleeve 16 to bone and tibial component 10. For example, exterior surface 32 can include projections to extend into bone or improve friction with bone. Also, interior channel 38 can include other features that permit sleeve 16 to attach to stem housing 24 in a coupled configuration, but that do not interfere with stem housing 24 in an un-coupled configuration. For example, interior channel can include a flange or lip that can snap into engagement with a mating flange or lip on stem housing 24 near bone-facing surface 18 (FIG. 1), but that does not contact stem housing 24 when sleeve 16 is slid further down stem housing 24. The flanges or lips can be crenelated or perforated to permit passage of bone cement. In another configuration, stem housing 24 can have a large diameter threaded portion near bone-facing surface 18 that can be threaded into engagement with a corresponding threaded portion on interior channel 38, and a small diameter portion that will disengage from the threaded portion on interior channel 38 when sleeve 16 is slid further down stem housing 24. In yet other examples, sleeve 16 can be threaded along stem housing 24 to vary a distance from bone-facing surface 18 to accommodate different length of L1.

Figure 8:
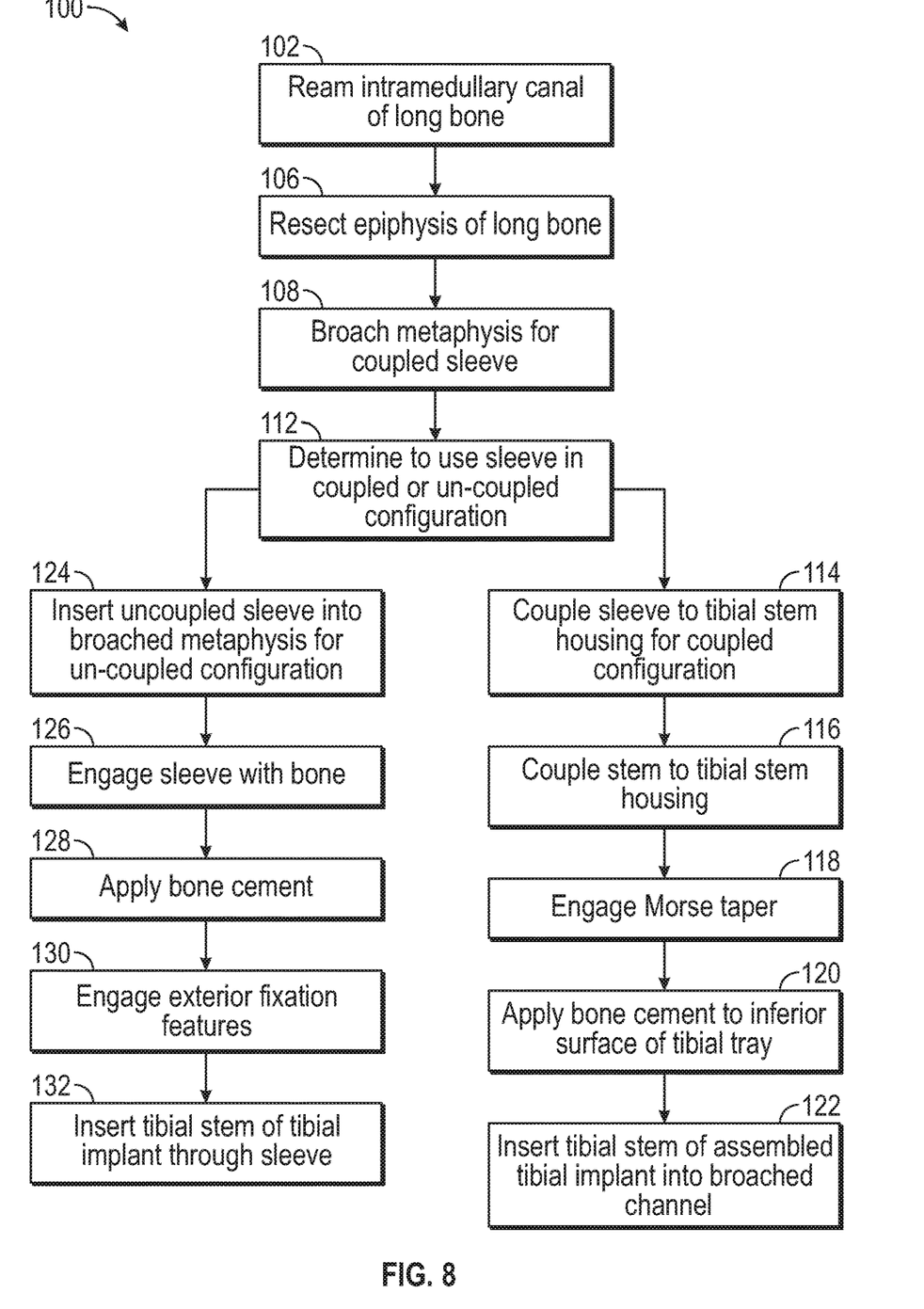
FIG. 8 is a line diagram illustrating steps of a method for implanting a tibial implant and a tibial sleeve in a tibia.

FIG. 8 is a line diagram illustrating steps of method 100 for implanting tibial component 10 (FIG. 1) and sleeve 16 (FIG. 1) or cone 80 (FIG. 6) in tibia T. Tibial component 10 can be implanted in a coupled and in an un-coupled configuration, as can be determined intraoperatively during an implantation procedure. At step 102, the intramedullary canal of a long bone can be reamed, after soft tissue is appropriately opened to expose the bone. The long bone can be reamed to receive an anchoring extension of a prosthetic implant, such as a stem. For example, intramedullary canal C of tibia T can be reamed to form reaming channel 54 that receives tibial stem 14, as shown in FIG. 3. At step 106, an end of the long bone can be resected, such as to engage flush with the prosthetic implant. For example, tibia T can be resected to form resected surface 70 that can engage with bone-facing surface 18 of tibial tray 12, as can be seen in FIG. 3. At step 108, the reamed channel in the long bone can be broached, such as to receive an additional anchoring component that can support the extension. For example, reaming channel 54 can be broached to form broaching channel 52 to receive sleeve 16, as shown in FIG. 2. At step 108, the broaching channel and position of the broach can be evaluated. The surgeon can visually inspect if the broach has passed beyond resected surface 70, for example. If the broach, e.g., broach 58, has passed further into the bone such that broach 58 is below resected surface 70, sleeve 16 can be used in an un-coupled state, or cone 80 can be used. If broach 58 is even with resected surface 70, sleeve 16 can be used in the coupled state. Broach 58 can have a height from its distal-most surface to its proximal-most surface that is approximately equal to the height of sleeve 16 between proximal portion 34 and distal portion 36 plus the height of gap G1, as shown in FIG. 4, when sleeve 16 is attached to stem housing 24. Thus, sleeve 16 can be used in the coupled or attached state when the top or proximal-most surface of broach 58 is approximately level with resected surface, which ensures that exterior surface 32 will adequately engage bone. In various examples, sleeve 16 can be used if the top of broach 58 is within 2.5 mm of resected surface, in the coupled state if within 0.5 mm and in the un-coupled state if within 2.5 mm. If the distance to the top of broach 58 exceeds 2.5 mm, a taller cone can be used or tibia T can be further resected.

The geometry of a void in the long bone produced by the reaming, broaching and resectioning of the long bone can also be evaluated if desired after broach 58 has been removed. For example, broaching channel 52 can be evaluated to determine the geometry of tapered portion 72 and longitudinal portion 74, as shown in FIG. 3. Evaluation of the bone geometry can be performed by visual inspection or by taking specific measurements of the resulting cavity formed by the reaming, broaching and resectioning. Measurement tools, such as depth gages, measuring sticks, measuring tape or probes can be used. In examples, measurements can be taken from images of the long bone taken using various imaging systems, such as x-ray systems, magnetic resonance imaging (MRI) systems and the like. Such measurements can be useful in determining the type or size of sleeve or cone to use.

At step 112, it can be determined if an additional anchoring component, such as a sleeve, are to be used in a coupled or un-coupled configuration, relative to an anchoring extension, such as a stem. More specifically, use of the coupled or un-coupled configurations can be based on the evaluation of the lengths of longitudinal (straight) and conical portions of the broached void geometry determined at step 108, which can be determined by or in conjunction with evaluating the depth of the broach in the bone relative to the resected surface. For example, the lengths L1 and L2 of longitudinal portion 74 and conical portion 72 can be determined. It can then be determined if sleeve 16 is to be attached to stem housing 24 before insertion into broaching channel 52 in the coupled configuration, or if sleeve 16 is first inserted into broaching channel 52 without coupling to stem housing 24 in the un-coupled configuration. If, for example, the broach is at the resected tibial surface, the coupled configuration can be used. If, for example, the broach 58 is below the resected surface, the un-coupled configuration can be used. If the broach 58 is below the surface, the tibia T can be further resected to the depth of broach 58.

At step 114, it can be determined that the depth of the broach 58 is at the tibial resection level 70 such that the anchoring component, such as a sleeve, will properly seat with broached bone. Thus, the anchoring component can be coupled to the anchoring extension. For example, sleeve 16 can be coupled to stem housing 24 if it is determined that sleeve 16 will properly mate with tapered portion 72 at the resected tibial surface 70. At step 116, e.g., sleeve 16 can be mated with the stem housing 24 in a coupled configuration such that the two components are rigidly attached. For example, sleeve 16 can be coupled to tibial tray 12, such as at stem housing 24. At step 118, the sleeve 16 can be mated with the stem housing 24 via a specific coupling mechanism. Specifically, a Morse taper or another coupling mechanism, such as a threaded coupling or the like, can be engaged to join the components. For example, sleeve 16 can be coupled to stem housing 24, such as via a Morse taper. At step 120, bone cement can be applied to the inferior bone facing surface 18 of the tibial implant at gap G1. Bone cement can also be added to the bottom of broaching channel 52 for engaging surface 36 at gap G2. It is desirable to avoid placing bone cement against tapered portion 72 in embodiments where sleeve 16 is made of porous material to avoid the bone cement preventing bone ingrowth. At step 122, the assembly of the anchoring extension and the anchoring component can be inserted into the broaching channel. For example, tibial stem 14 and sleeve 16 which are attached to tibial component 10 can be inserted into reaming channel 54 and broaching channel 52 such that exterior surface 32 engages tapered portion 72. As such, tibial component 10 can be seated within tibia T and the implant operation can proceed.

At step 124, if the broach 58 is seated below the tibial surface 70, then the anchoring component will not properly seat with broached bone. Thus, the anchoring component can be employed un-coupled from the anchoring extension. For example, sleeve 16 can be employed un-coupled from stem housing 24 if it is determined that sleeve 16 will not properly mate with tapered portion 72. In particular, if tapered portion 72 is too deep and sleeve 16 remains attached to stem housing 24 of tibial tray 12, exterior surface 32 of sleeve 16 won't be far down enough within broaching channel 52 to engage tapered portion 72. Alternatively, a different anchoring component, such as cone 80, or a different sized anchoring component, such as a taller cone 80, can be used based on evaluation of tapered portion 72 and longitudinal portion 74.

As step 126, an anchoring component can be positioned within the bone void and mated with bone in an un-coupled configuration, e.g., without being attached to an anchoring extension. The anchoring component can be mated with the bone such that the anchoring component is immobilized within the long bone. For example, sleeve 16 can be pushed up against bone forming tapered portion 72. Sleeve 16 can be pressed firmly against the bone so as to be immobilized. In other examples, cone 80 can be used for the un-coupled configuration.

At step 128, bone cement can be applied to the G1 and G2 voids in the bone produced by the broaching. Specifically, bone cement can be applied to longitudinal portion 74. Thus, any indentations of surface 34 of the anchoring device can be filled with bone cement to aid the anchoring process. The bone cement can be applied to secure sleeve 16 within broaching channel 52, such as by providing anti-rotation anchoring.

At step 130, the additional exterior fixation features of the anchoring component can be utilized to facilitate fixation of sleeve 16 to bone, before or after bone cement is applied. For example, a porous exterior surface of sleeve 16 can be pressed into the bone before bone cement is applied. Additionally, sleeve 16 can be provided with anchoring features such as protrusions, like spikes, to be pushed into the bone. Furthermore, the exterior fixation features can comprise voids or spaces in the anchoring component that can be filled with bone cement to facilitate fixation and immobilization of the anchoring component within the bone. For example, indentations 84A and 84B of sleeve 16 can be filled with bone cement.

At step 132, the anchoring extension can be positioned relative to the anchoring component within the bone. The anchoring extension can be inserted through the anchoring component and the broaching channel and down into a reaming channel. For example, tibial stem 14 can be coupled to tibial tray 12 and inserted through sleeve 16. More specifically, tibial stem 14 can be inserted through interior channel 38 into reaming channel 54 and stem housing 24 can be inserted into sleeve 16 at interior channel 38 such that stem housing 16 and interior channel 38 partially overlap but do not engage. Thus, stem housing 24 can be inserted into broaching channel 52 such that exterior surface 32 will be spaced from tapered portion 72, but bone cement can be filled into voids therebetween to immobilize sleeve 16. As such, tibial component 10 can be affixed to tibia T.

VARIOUS NOTES & EXAMPLES

Example 1 can include or use subject matter such as a prosthetic implant system for at least partially reconstructing a knee joint, the prosthetic implant system can comprise: a prosthetic implant and a sleeve. The prosthetic implant can comprise a tibial tray component for at least partially reconstructing a tibia of the knee joint, and a stem configured to extend from the tibial tray component to anchor the tibial tray component in the tibia of the knee joint. The sleeve can comprise an outer wall configured to engage with bone, and an inner bore configured to receive the stem. The inner bore can be shaped to couple to the prosthetic implant at a first location proximate the tibial tray component while surrounding at least a portion of the stem, and uncouple from the prosthetic implant at a second location spaced from the first location while still surrounding at least a portion of the stem.

Example 2 can include, or can optionally be combined with the subject matter of Example 1, to optionally include a tibial tray component that can further comprise a stem housing configured to receive the stem.

Example 3 can include, or can optionally be combined with the subject matter of one or any combination of Examples 1 or 2 to optionally include an inner bore and an outer surface of the stem housing that can be shaped to have a Morse taper interface at the first location.

Example 4 can include, or can optionally be combined with the subject matter of one or any combination of Examples 1 through 3 to optionally include an inner bore and an outer surface of the stem housing that can be shaped to flushly engage at the first location and to be spaced apart at the second location.

Example 5 can include, or can optionally be combined with the subject matter of one or any combination of Examples 1 through 4 to optionally include an inner bore that can comprise a cylindrical through-bore having a diameter larger than the stem housing.

Example 6 can include, or can optionally be combined with the subject matter of one or any combination of Examples 1 through 5 to optionally include an outer wall that can include fixation features.

Example 7 can include, or can optionally be combined with the subject matter of one or any combination of Examples 1 through 6 to optionally include fixation features that can comprise indentations is a surface of the sleeve configured to face toward the tibial tray component.

Example 8 can include, or can optionally be combined with the subject matter of one or any combination of Examples 1 through 7 to optionally include indentations that can be claw-shaped.

Example 9 can include, or can optionally be combined with the subject matter of one or any combination of Examples 1 through 8 to optionally include fixation features that can comprise protrusions for frictionally engaging bone.

Example 10 can include, or can optionally be combined with the subject matter of one or any combination of Examples 1 through 9 to optionally include a sleeve that can comprise a porous metal structure.

Example 11 can include or use subject matter such as a method of implanting an implant including a stem. The method can comprise reaming an intramedullary canal of a long bone to form a channel, resecting an epiphysis portion of the long bone to form a resected surface, broaching a proximal end of the long bone to form a broached channel, evaluating a depth of the broach below the resected surface, determining to use a stem sleeve in a coupled or un-coupled state based on the depth of the broach, inserting the stem sleeve into the broached channel for the un-coupled state or attaching the stem sleeve onto the stem of the implant for the coupled state, and inserting the implant into the broached channel.

Example 12 can include, or can optionally be combined with the subject matter of Example 11, to optionally include a broached channel that can comprise a distal taper portion, and a proximal longitudinal portion.

Example 13 can include, or can optionally be combined with the subject matter of one or any combination of Examples 11 or 12 to optionally include evaluating the depth of the broach that can comprise determining visibility of the proximal longitudinal portion above the broach.

Example 14 can include, or can optionally be combined with the subject matter of one or any combination of Examples 11 through 13 to optionally include a stem sleeve that can be positioned to at least partially surround a stem housing that receives the stem in the coupled state and the un-coupled state.

Example 15 can include, or can optionally be combined with the subject matter of one or any combination of Examples 11 through 14 to optionally include disposing bone cement within the broached channel between a proximal surface of the sleeve and a distal surface of the tibial implant within the proximal longitudinal portion.

Example 16 can include, or can optionally be combined with the subject matter of one or any combination of Examples 11 through 15 to optionally include disposing bone cement within the broached channel between concentric surfaces of the tibial implant and the sleeve within the distal taper portion.

Example 17 can include, or can optionally be combined with the subject matter of one or any combination of Examples 11 through 16 to optionally include inserting the tibial stem sleeve into the broached channel that can comprise engaging bone within the distal taper portion of the broached channel with the tibial stem sleeve, and inserting the tibial implant into the broached channel that can comprise leaving a space between an inner bore in the tibial stem sleeve and the tibial stem.

Example 18 can include, or can optionally be combined with the subject matter of one or any combination of Examples 11 through 17 to optionally include engaging bone within the distal taper portion of the broached channel with the tibial stem sleeve that can comprise engaging a porous structure of an outer wall of the tibial stem sleeve with the bone.

Example 19 can include, or can optionally be combined with the subject matter of one or any combination of Examples 11 through 18 to optionally include disposing bone cement within fixation features located on a proximal surface of the tibial stem sleeve.

Example 20 can include, or can optionally be combined with the subject matter of one or any combination of Examples 11 through 19 to optionally include attaching the stem sleeve onto the stem of the implant that can comprise engaging a Morse taper between an inner bore in the tibial stem sleeve and the tibial implant, and inserting the tibial implant into the broached channel that can comprise engaging the tibial stem and the tibial stem sleeve with bone inside the broached channel.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of intraoperatively evaluating a tibia for implanting a tibial component of a prosthetic knee device; the method comprising:
    planning a procedure to use a stem sleeve coupled to a tibial stem to engage a broached channel;
    reaming an intramedullary canal into a proximal end of a tibia to form a channel;
    resecting a proximal portion of the tibia to form a planar resected surface;
    broaching the channel to form a broached channel such that a top of the broached channel is located a distance below the planar resected surface;
    evaluating if the distance is sufficiently small to support using a stem sleeve in a coupled state;
    determining that the distance is too large to support using the stem sleeve in a coupled state; and
    inserting the stem sleeve into the broached channel to engage the broached channel; and
    positioning the tibial stem through the stem sleeve such that there is a gap between the tibial stem and the stem sleeve;
    wherein evaluating if the distance is sufficiently small comprises evaluating if the stem sleeve can simultaneously engage the broached channel and the stem of the tibial component when engaged with a bottom of the broached channel.

2. The method of claim 1, further comprising broaching the channel to form a distal taper portion configured to engage the broached channel, the distal taper portion forming the top of the broached channel.

3. The method of claim 2, wherein broaching the channel to form the broached channel comprises broaching the channel to form a proximal longitudinal portion that positions the distal taper portion below the planar resected surface by the distance.

4. The method of claim 1, wherein inserting the stem sleeve into the broached channel further comprises disposing bone cement within the proximal longitudinal portion.

5. The method of claim 1, further comprising:
using the stem sleeve in a coupled state when the distance is in the range of 0 mm to 0.5 mm; and
using the stem sleeve in an un-coupled state when the distance is greater than 0.5 mm up to 2.5 mm.

6. A method of intraoperatively switching between using a tibial component sleeve and a tibial component cone for implanting a tibial component of a prosthetic knee device during a procedure, the method comprising:
reaming an intramedullary canal in a proximal end of a tibia to form a channel;
resecting a proximal portion of the tibia to form a planar resected surface commensurate with using a sleeve;
broaching the channel to form a broached channel such that a top of the broached channel is located a distance below the planar resected surface;
determining that the broached channel is inappropriate for using a sleeve attached to the tibial component to engage the broached channel by determining that bone quality in the broached channel proximate the planar resected surface is poor or determining that the broached channel is located too far below the planar resected surface; and
inserting a cone into the broached channel to engage the broached channel below the planar resected surface without resecting additional bone; and
inserting the tibial component into the channel without engaging the cone.

7. The method of claim 6, further comprising:
intraoperatively having a cone and a sleeve ready and available at a beginning of the procedure.

8. A method of implanting an implant including a stem, the method comprising:
reaming an intramedullary canal of a long bone to form a channel;
resecting an epiphysis portion of the long bone to form a resected surface;
broaching a proximal end of the long bone to form a broached channel;
evaluating a depth of the broach below the resected surface;
determining to use a stem sleeve in a coupled or un-coupled state based on the depth of the broach, wherein the stem sleeve comprises:
a proximal surface;
a distal surface;
an exterior surface connecting the proximal surface and the distal surface an inner bore connecting the proximal surface and the distal surface within the exterior surface, the inner bore defining a Morse taper; and
a plurality of indentations in the proximal surface having a shape to prevent rotation of the stem sleeve when filled with bone cement;
inserting the stem sleeve into the broached channel for the un-coupled state or attaching the stem sleeve onto the stem of the implant for the coupled state; and
inserting the implant into the broached channel; wherein:
the stem sleeve is implanted in a coupled state when the depth is in the range of 0 mm to 0.5 mm; and
the stem sleeve is implanted in an un-coupled state when the depth is greater than 0.5 mm up to 2.5 mm.

9. The method of claim 8, wherein the broached channel comprises:
a distal taper portion; and
a proximal longitudinal portion.

10. The method of claim 9, wherein evaluating the depth of the broach comprises determining visibility of the proximal longitudinal portion above the broach.

11. The method of claim 9, wherein the stem sleeve is positioned to at least partially surround a stem housing that receives the stem in the coupled state and the un-coupled state.

12. The method of claim 9, further comprising disposing bone cement within the broached channel between the proximal surface of the sleeve and a distal surface of the tibial implant within the proximal longitudinal portion.

13. The method of claim 9, further comprising disposing bone cement within the broached channel between concentric surfaces of the tibial implant and the sleeve within the distal taper portion.

14. The method of claim 9, wherein:
inserting the tibial stem sleeve into the broached channel comprises engaging bone within the distal taper portion of the broached channel with the tibial stem sleeve; and
inserting the tibial implant into the broached channel comprises leaving a space between the inner bore in the tibial stem sleeve and the tibial stem.

15. The method of claim 14, wherein engaging bone within the distal taper portion of the broached channel with the tibial stem sleeve comprises engaging a porous structure of the exterior surface of the tibial stem sleeve with the bone.

16. The method of claim 8 further comprising disposing bone cement within the indentations of the tibial stem sleeve.

17. The method of claim 8, wherein:
attaching the stem sleeve onto the stem of the implant comprises engaging the Morse taper with the stem of the tibial implant; and
inserting the tibial implant into the broached channel comprises engaging the tibial stem and the tibial stem sleeve with bone inside the broached channel.

18. The method of claim 16, further comprising preventing rotation of the stem sleeve relative to the tibial tray by disposing bone cement within claw-shaped indentations.

19. The method of claim 8, further comprising leaving the stem sleeve and the implant in the long bone in either the coupled state or the un-coupled state after the method of implanting is completed.

* * * * *

UNITED STATES PATENT AND TRADEMARK OFFICE
CERTIFICATE OF CORRECTION

PATENT NO. : 10,987,225 B2
APPLICATION NO. : 16/047463
DATED : April 27, 2021
INVENTOR(S) : Yoko et al.

Page 1 of 1

It is certified that error appears in the above-identified patent and that said Letters Patent is hereby corrected as shown below:

In the Claims

In Column 14, Line 37, in Claim 1, delete "device;" and insert --device,-- therefor Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*